US011070745B2

(12) United States Patent
Hale (10) Patent No.: US 11,070,745 B2
(45) Date of Patent: Jul. 20, 2021

(54) AUTOMATIC IMAGE ORIENTATION BASED ON USE (71) Applicant: KARL STORZ Imaging, Inc., Goleta, CA (US)

(72) Inventor: Eric L Hale, Vancouver, WA (US)

(73) Assignee: KARL STORZ Imaging, Inc., Goleta, CA (US)

(*) Notice: Subject to any disclaimer, the term of this patent is extended or adjusted under 35 U.S.C. 154(b) by 0 days.

(21) Appl. No.: 16/665,706

(22) Filed: Oct. 28, 2019

(65) Prior Publication Data
US 2021/0127074 A1 Apr. 29, 2021

(51) Int. Cl.
| | |
|---|---|
| *A61B 1/00* | (2006.01) |
| *H04N 5/262* | (2006.01) |
| *H04N 7/18* | (2006.01) |
| *H04N 5/225* | (2006.01) |
| *A61B 1/045* | (2006.01) |
| *A61B 90/00* | (2016.01) |
| *G06N 3/08* | (2006.01) |

(52) U.S. Cl.
CPC ....... *H04N 5/2628* (2013.01); *A61B 1/00006* (2013.01); *A61B 1/00045* (2013.01); *A61B 1/045* (2013.01); *A61B 90/361* (2016.02); *H04N 5/2253* (2013.01); *H04N 7/183* (2013.01); *A61B 1/00174* (2013.01); *A61B 1/00179* (2013.01); *A61B 2090/364* (2016.02); *G06N 3/08* (2013.01); *H04N 2005/2255* (2013.01)

(58) Field of Classification Search
CPC ............ A61B 1/00045; A61B 1/00174; A61B 1/00179; G02B 23/2415; G06T 2207/10068; H04N 5/23296
See application file for complete search history.

(56) References Cited

U.S. PATENT DOCUMENTS

| | | | |
|---|---|---|---|
| 5,582,576 A | * | 12/1996 | Hori ................... A61B 1/00096 600/118 |
| 6,241,657 B1 | | 6/2001 | Chen |
| 6,346,940 B1 | | 2/2002 | Fukunaga |

(Continued)

FOREIGN PATENT DOCUMENTS

| | | |
|---|---|---|
| WO | 9501749 A1 | 1/1995 |
| WO | 2010129324 A2 | 11/2010 |

OTHER PUBLICATIONS

Google Search for NPL; 2021. (Year: 2021).*

(Continued)

*Primary Examiner* — Luis Perez-Fuentes
(74) *Attorney, Agent, or Firm* — Michael Loi; Honigman LLP (57) ABSTRACT A video imaging system is provided. The video imaging system is configured to maintain a video image displayed on a display unit in a predetermined orientation based upon a use. The video imaging system includes an endoscope, a camera head unit, a camera control unit configured to determine a focal distance, and a display control unit. The display control unit is configured to process the focal distance to determine a use. The use is processed by the display control unit so as to maintain the video image in the predetermined orientation. The contextual information may be focal distance, image data or endoscopic orientation.

18 Claims, 5 Drawing Sheets

(56) References Cited

U.S. PATENT DOCUMENTS

| | | | |
|---|---|---|---|
| 6,471,637 B1* | 10/2002 | Green | A61B 1/00045 |
| | | | 600/109 |
| 6,511,418 B2 | 1/2003 | Shahidi | |
| 6,663,559 B2 | 12/2003 | Hale | |
| 6,916,286 B2 | 7/2005 | Kazakevich | |
| 7,585,273 B2 | 9/2009 | Adler | |
| 7,824,328 B2 | 11/2010 | Gattani | |
| 7,956,887 B2 | 6/2011 | Hoeg | |
| 8,911,358 B2* | 12/2014 | Koninckx | A61B 1/00181 |
| | | | 600/113 |
| 8,982,203 B2* | 3/2015 | Berci | A61B 1/00163 |
| | | | 348/74 |
| 9,375,133 B2 | 6/2016 | Kitamura | |
| 10,413,155 B2* | 9/2019 | Inoue | A61B 5/065 |
| 10,419,680 B2* | 9/2019 | Inoue | H04N 5/23293 |
| 2002/0055669 A1* | 5/2002 | Konno | A61B 1/051 |
| | | | 600/167 |
| 2002/0161280 A1 | 10/2002 | Chatenever et al. | |
| 2005/0228230 A1 | 10/2005 | Schara et al. | |
| 2012/0130159 A1* | 5/2012 | Abri | A61B 1/00149 |
| | | | 600/102 |
| 2013/0038708 A1 | 2/2013 | Iwasaki | |
| 2014/0210974 A1* | 7/2014 | Yoshino | G02B 23/2438 |
| | | | 348/65 |
| 2019/0265490 A1* | 8/2019 | Duckett, III | A61B 1/00105 |

OTHER PUBLICATIONS

Multifunctional endoscopic system for support of early cancer diagnosis; Gono—2008. (Year: 2008).*
Artikis, T. Extended European Search Report, dated Feb. 18, 2021 pp. 1-6, Munich, Germany Application No. 20204122.4-1122.

* cited by examiner

AUTOMATIC IMAGE ORIENTATION BASED ON USE

TECHNICAL FIELD

This disclosure relates to a camera configured to automatically orient an image based upon use.

BACKGROUND

Video cameras provide a video image based upon the orientation of the camera. In some embodiments, the physical dimension of the camera provides the user with a visual indicator to ensure the video image is oriented in a desired orientation. For instance, it is easy to capture a video image from a cuboidal shaped video camera in a predetermined orientation as it is easily recognizable when the camera is upright. However, in certain applications, such as an endoscope, it is difficult to determine when the endo scope is upright as the endo scope is generally cylindrical. Further, the orientation of the video image may rotate when the endo scope is handed from one person or another, such as from the nurse to the surgeon.

Figure 1A:
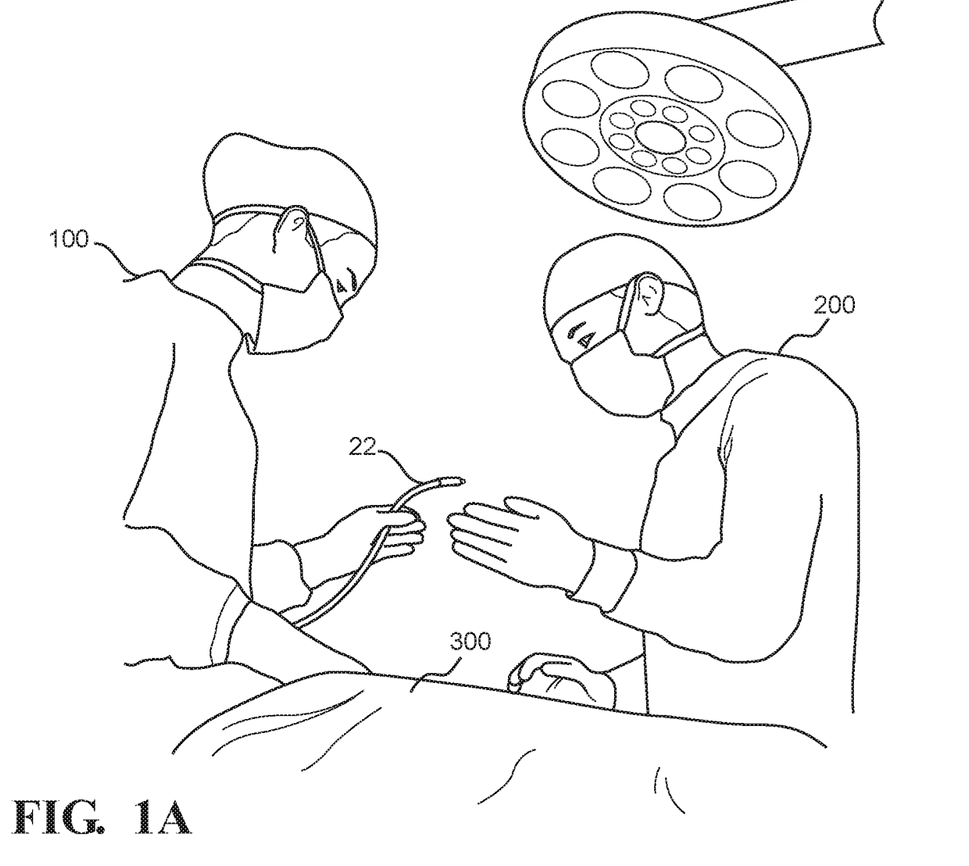
FIG. 1A is a depiction showing a nurse holding an endoscope in a surgery room.
Figure 1B:
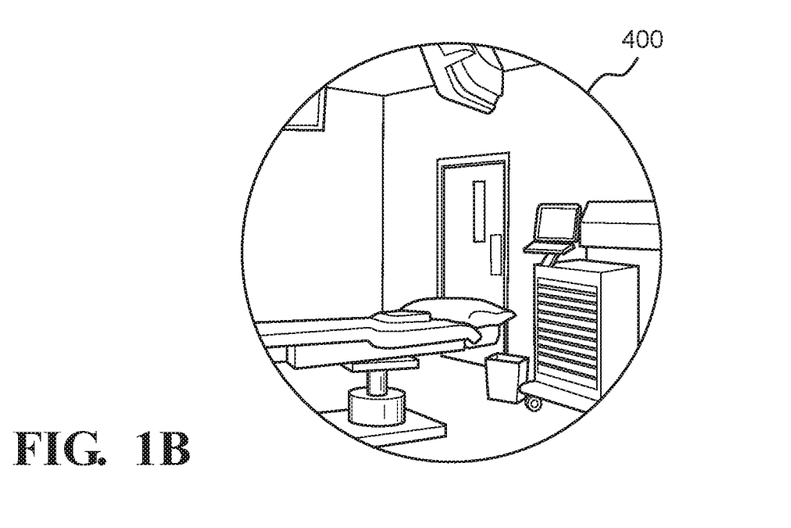
FIG. 1B is a depiction of an image of the endoscope shown in FIG. 1A.

An example will be described with reference to FIGS. 1A-2B. FIG. 1A depicts a surgical procedure with a nurse 100 and a doctor 200 standing over a patient 300. FIG. 1A shows the nurse 100 holding the endoscope 22. The nurse 100 turns on the endoscope 22 and currently levels the endoscope 22. As used herein, the term level means rotating the video image 400 on the display to a desired orientation. The nurse 100 may rotate the grip of the endo scope 22 to orient the imager in an upright orientation so that outside of the surgical site, the video image is aligned with the orientation of the physical space. That is, the doors and walls of the video image 400 are upright as is seen by the nurse 100 and the surgeon 200, as shown in FIG. 1B. Alternatively, an actuator, such as a button, may be pressed to rotate the video image 400.

Figure 2A:
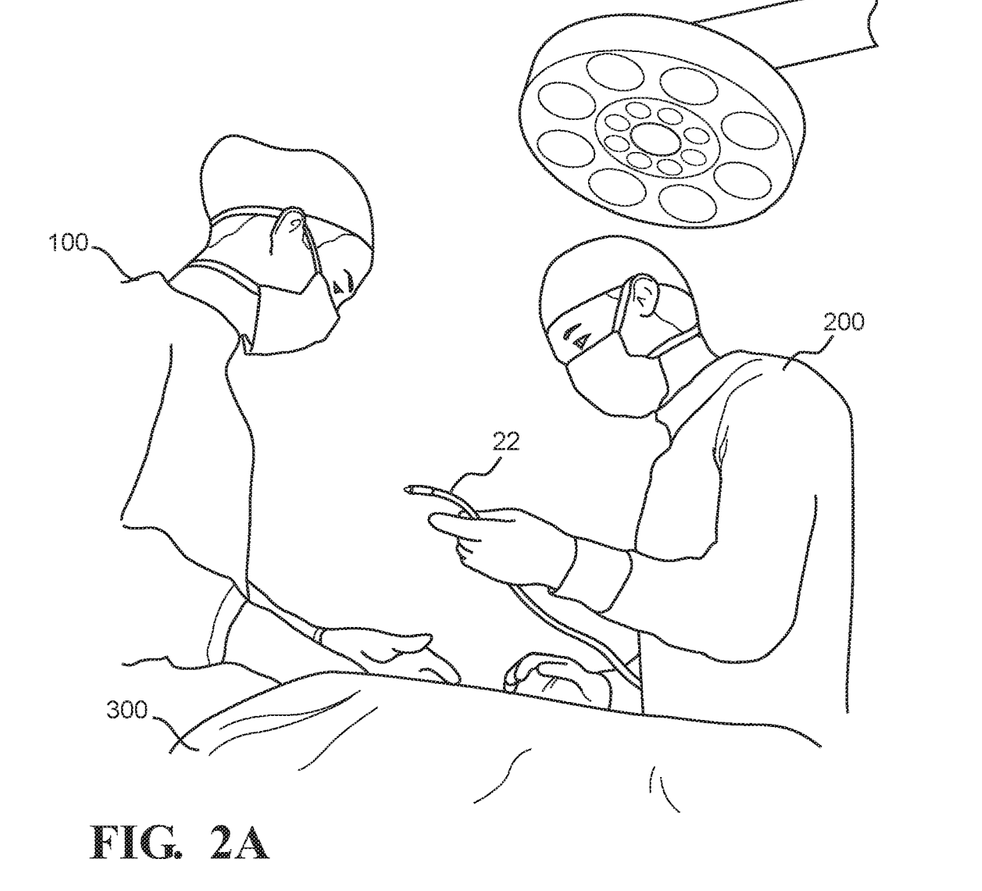
FIG. 2A is a depiction showing a surgeon holding the endoscope.
Figure 2B:
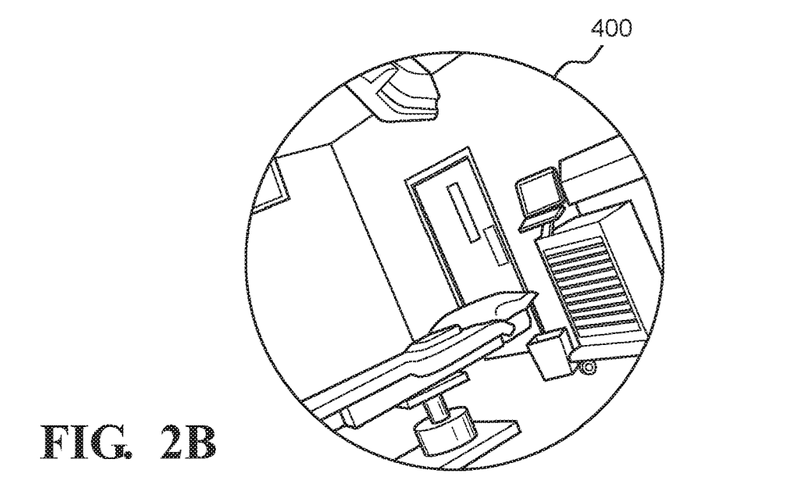
FIG. 2B is a depiction of an image of the endoscope shown in FIG. 2A.

FIG. 2A is a depiction of FIG. 1A after the nurse 100 has handed the endoscope to the surgeon 200. When the endoscope 22 is handed over, the surgeon 200 may grip the endoscope 22 in a different orientation, which rotates the video image, as shown in FIG. 2B. Thus, the surgeon 200 has to rotate the endoscope 22 within his/her grip to orient the video image 400 to align with the physical orientation of the room, or press the actuator as the case may be so as to level the video image 400 to a desired orientation, or the orientation shown in FIG. 1B.

Further, the orientation of the video image 400 of the surgical site may rotate as the surgeon 200 manipulates the endoscope within the surgical site. Such a change in the video image 400 requires the surgeon 200 to correlate what is seen on the display with the actual position of the endoscope 22.

Accordingly, it remains desirable to have an imaging system configured to automatically orient the video image to a desired orientation.

SUMMARY

One aspect of the disclosure provides an imaging system configured to orient an image based upon use of the imagine system. The imaging system includes a camera head unit, a light source and a display control unit. The camera head unit includes a camera head and a camera control unit. The camera head unit is configured to obtain image data and process the image data into an image signal. The camera head includes an image sensor. A light source generates electromagnetic radiation which is captured by the image sensor in the form of image data.

The camera head may be coupled to an endoscope. A display control unit is further configured to process the focal distance to determine a use, and process the image so as to display the image onto a display unit in an orientation associated with the determined use. The use may be a surgical use or a non-surgical use. In some implementations, the imaging system is a video imaging system, such that the image signal is a video signal.

In some aspects of the imaging system, the imaging system includes an orientation unit is configured to detect at least one of an acceleration and a gravitational relationship of the endoscope. The orientation unit may be disposed in the camera head unit. The orientation unit may include an accelerometer or a gyroscope sensor. The orientation unit detects an acceleration and/or a gravitational relationship of the camera and transmits the detected acceleration and/or gravitational relationship to the display control unit. The display control unit processes the acceleration and/or gravitational relationship to determine a use.

In another aspect of the imaging system, the display control unit processes an acceleration and/or a gravitational relationship along with a focal distance to determine a use.

In another aspect of the imaging system, additional contextual information is provided to further identify the type of surgical use. The imaging system may include a database storing a plurality of surgical procedures. The surgical procedures may include contextual information relating to the corresponding procedure to include image data and ranges for endoscopic orientation. Each surgical procedure is also associated with a predetermined image orientation. The predetermined image orientation may include a predetermined video image orientation.

Image data may include anatomical features such as a meniscus, a labrum or the like. The endoscopic orientation may be determined by the processing information gathered by the orientation unit. The contextual information may be processed by the display control unit to determine which surgical procedure in the database is being performed and to process the image (e.g., the video image) so as orient, maintain and display the image in the predetermined image orientation.

In another aspect of the present disclosure, the imaging system includes an input. The input is configured to select any one of the plurality of surgical procedures stored in the database. In such an embodiment, the display control unit automatically orients the image signal (e.g., the video signal) so as to maintain the image (e.g., the video image) in an orientation corresponding to the selected surgical procedure.

In another aspect of the present disclosure, the display control unit may be programmed with a neural network for learning.

In another aspect of the present disclosure, the video imaging system may further include a second input configured to adjust the orientation of the image (e.g., the video image) displayed on the display unit.

In yet another aspect of the present disclosure, a method for displaying a video image onto a display is provided. The method includes determining, with a camera control unit, a focal distance. The method also includes processing, with a display control unit, the focal distance so as to determine a use. The method further includes processing, with the display control unit, the use to maintain the video image in a predetermined orientation.

This aspect may include one or more of the following features. In some implementations, a camera head unit includes a lens and an image sensor. The method may include moving the lens relative to the image sensor. The method may also include controlling, with the camera head unit, a displacement of the image sensor relative to the lens so as to focus the video image when there is a change in the focal distance.

In some implementations, the method includes detecting, with an orientation unit, at least one of an acceleration and a gravitational relationship of an endoscope. The method may also include processing, with the display control unit, the at least one of the acceleration and the gravitational relationship of the endoscope so as to determine the use.

In some implementations, the method includes storing, in a database, a plurality of surgical procedures, each of the plurality of surgical procedures having a video predetermined orientation, and each of the plurality of surgical procedures being a surgical use.

In some implementations, each of the plurality of surgical procedures stored in the database includes contextual information including an image data.

In some implementations, the method includes processing, with the display control unit, image data with the video image. The method may also include determining, with the display control unit, which of the surgical procedures of the plurality of surgical procedures is being performed. The method may further include processing, with the display control unit, the video image so as to maintain the video image in the predetermined video orientation.

In some implementations, the method includes processing, with the camera head unit, a range for an endoscopic orientation. The method may also include processing, with the camera head unit, the at least one of the acceleration and the gravitational relationship of the endoscope so as to determine an endoscopic orientation. The method may further include processing, with the display control unit, the endoscopic orientation to determine a surgical procedure.

The details of one or more implementations of the disclosure are set forth in the accompanying drawings and the description below. Other aspects, features, and advantages will be apparent from the description and drawings, and from the claims.

DESCRIPTION OF DRAWINGS

Like reference symbols in the various drawings indicate like elements.

DETAILED DESCRIPTION

A video camera configured to automatically orient a video image based upon a determined use of the video camera is provided. A display control unit processes contextual information such as focal distance, image data and endoscopic orientation to determine a use. The use is processed by the computer processing unit so to maintain the video image in a predetermined orientation. Accordingly, the video camera automatically orients the video image based upon the determined use.

Figure 3:
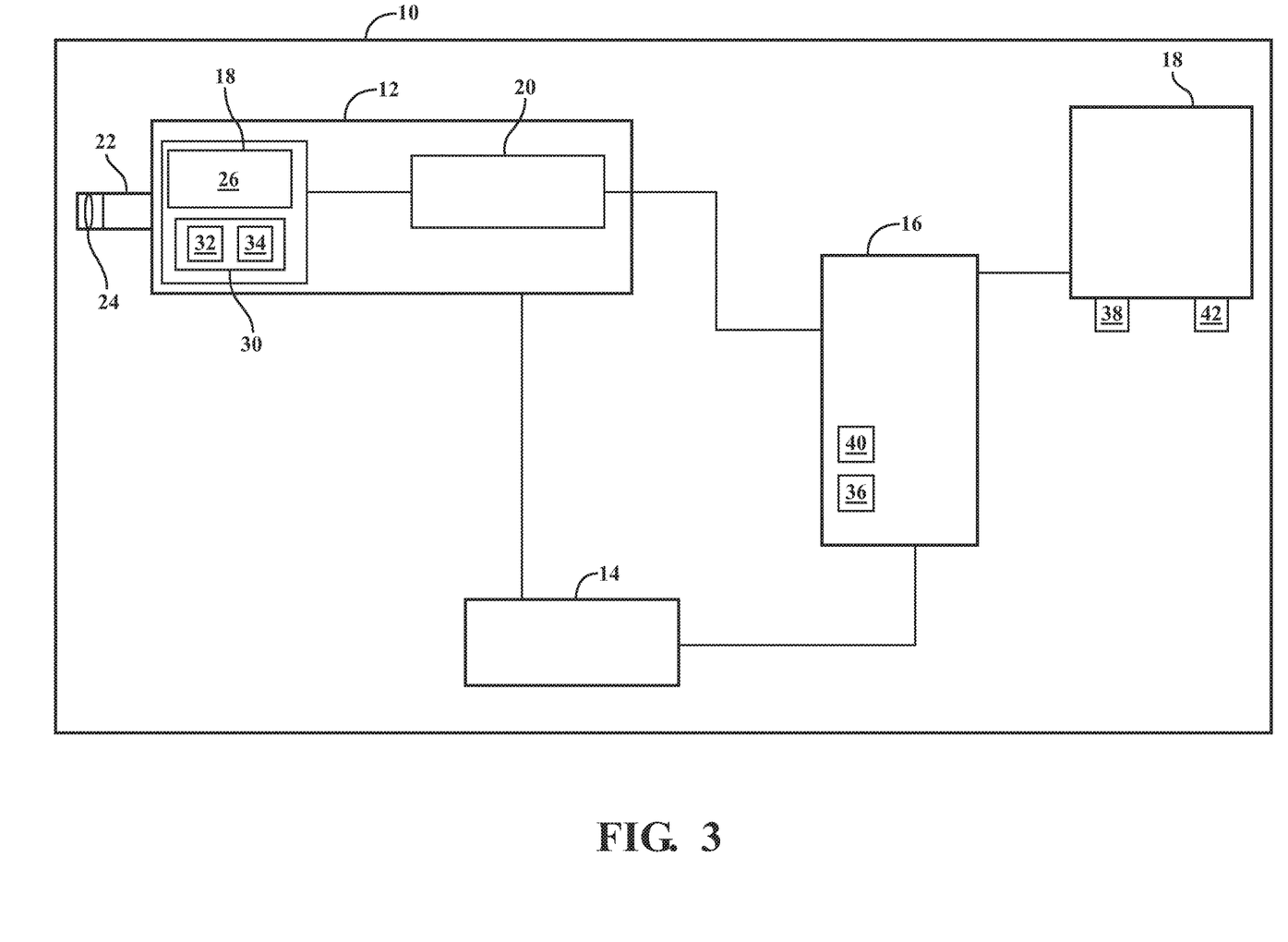
FIG. 3 is a schematic view of a camera according to the principles of the present disclosure.

With reference now to FIG. 3, an illustrative depiction of a video imaging system 10 is provided. The video imaging system 10 includes a camera head unit 12, a light source 14 and a display control unit 16. The camera head unit 12 includes a camera head 18 and a camera control unit 20. The camera head unit 12 is configured to obtain image data and process the image data into a video signal, as explained in greater detail below. The camera head 18 is coupled to an endoscope 22 by optics including a plurality of lenses 24. The camera head 18 includes an image sensor 26. For illustrative purposes, a description of the video imaging system 10 is provided within the context of an endoscope 22. However, it should be appreciated that other scopes may be used, illustratively including an exoscope, borescopes and the like. The image sensor 26 may be disposed within the endoscope 22, for example, adjacent to or in place of the lens 24 as in a video endoscope. Similarly, while a video imaging system 10 is generally shown and described herein, it should be appreciated that other imaging systems (e.g., still imaging systems having still cameras capturing still images) may be used.

The light source 14 generates electromagnetic radiation which is captured by the image sensor 26 in the form of image data. The light source 14 may be formed by one or more Light Emitting Diodes (LED) within an external light source housing providing "cold light" transmitted via optical fiber connection to the endoscope 22 as is known in the art.

The camera head 18 is in communication with the camera control unit 20 through either a cable or a wireless connection. The camera control unit 20 controls various processing functions of the camera head unit 12 to include timing of the light source 14, readout of the image sensor 26 and the like. The image sensor 26 functions in coordination with the light source 14 to gather image data which is processed by the camera control unit 20 to output a video signal. The video signal is processed by the display control unit 16. The display control unit 16 processes the video signal for display onto a display unit 28. The endoscope 22 and camera head 18 may form an integral unit or may be detached from each other as singular functional pieces. Regardless of the specific configuration, the principles of the present disclosure apply to various examples of video imaging systems 10.

The image sensor 26 can be a complementary metal oxide semiconductor "CMOS" or a charged coupled device "CCD". It should be appreciated that any pixelated image sensor 26 currently known or later developed may be modified and adopted for use herein. In one embodiment, the image sensor 26 is configured to receive electromagnetic radiation in the visible spectrum and also in the infrared range between about 800 nanometers to 1200.

In another aspect, the video imaging system 10 may include a pair of image sensors 26, wherein one of the image sensors 26 is configured to receive electromagnetic radiation in the visible spectrum with a particular field of view and the other of the image sensors 26 is configured to receive electromagnetic radiation in the infrared range between about 800 nanometers to 1200 nanometers. One skilled in the art would recognize that various systems using combinations of one or more image sensors 26 may benefit from the principles of the present disclosure. The endo scope 22 outputs the video image onto a display unit 28.

In one aspect of the video imaging system 10, a focal distance of the camera unit may be processed by the display control unit 16 to determine a use. Alternatively, the display control unit 16 may process the focal distance along with other contextual information so as to determine the use. As used herein, the term "focal distance" refers to a distance that an object appears to be from a lens (e.g., lens 24) when in focus. For illustrative purposes, a short focal distance shall refer to a video image of an object 10 cm or less from the lens 24 whereas a long focal distance refers to a video image of an object farther than 10 cm. It should be appreciated that the provided length of a short focal distance and long focal distance is exemplary and is not limiting to the scope of the appended claims.

The spatial displacement may be achieved manually or automatically. For instance, in a camera head unit 12 with a manual focus, the spatial displacement may be determined based upon the displacement of the image sensor 26 with respect to a fixed lens 24, a displacement of a lens 24 with respect to a fixed image sensor 26 or a displacement of both a moveable lens 24 and a moveable image sensor 26. Displacement of the lens 24, image sensor 26 or both may be achieved using known mechanical and electro-mechanical actuators and drives which may be controlled by a dial or a button disposed on the endoscope 22 or automatically in the case of auto-focus. Signals from the dial or button, as the case may be, may be processed by the camera control unit 20 to move the lens 24 and/or the image sensor 26. The adjustment processed by the camera control unit 20 may be transmitted to the display control unit 16 to determine the use.

For example, the display control unit 16 may determine that the endoscope is in a non-surgical use when the distance between the lens 24 and the image sensor 26 is at its shortest distance, placing the focus at infinity and thus, focal distance is long. Alternatively, the display control unit 16 may determine that the camera is in a surgical use when the distance between the lens 24 and the image sensor 26 is at its greatest distance, and the focal distance is short. It should be appreciated that the display control unit 16 may be programmed to determine a long or short focal distance based upon a range of distance between the lens 24 and the image sensor 26. For illustrative purposes, a long focal distance is commensurate with the endoscope 22 operating outside of the body, and is determined by a distance between the lens 24 and the image sensor 26 that is below a predetermined distance. A short focal distance is commensurate with the endo scope 22 operating inside of the body, and is determined by a distance between the lens 24 and the image sensor 26 that is greater than or equal to the predetermined distance.

As used herein, non-surgical use refers to an instance where the endoscope 22 is operating outside of the body. In such an instance, the display control unit 16 processes the video signal such that the video image displayed on the display unit 28 is oriented in an upright position. As used herein, upright refers to a vertical axis with respect to the horizon. Thus, the video imaging system 10 may use the focal distance to automatically orient the video image displayed on the display unit 28 in an upright position which allows for (i) rotation of the endoscope 22 as it is passed outside of the patient's body from one user to the other, or (ii) rotation of the endoscope 22 by a single user. In another example, the camera head unit 12 may be equipped with an automatic zoom function, wherein displacement of lens 24 with respect to image sensor 26 is made automatically.

The video imaging system 10 may further include an orientation unit 30. The orientation unit 30 may be disposed in the camera head unit 12. The orientation unit 30 is configured to detect at least one of an acceleration and a gravitational relationship of the endoscope 22. For example, the orientation unit 30 may include an accelerometer 32. Any accelerometer 32 currently known and/or or later developed may be adapted for use herein, illustratively including a device commonly known as a micromachined microelectromechanical system. The accelerometer 32 may be mounted to the camera head unit 12 and may detect an acceleration of the camera made in reference to the Earth's gravity.

In another example of an orientation unit 30, the orientation unit 30 includes a gyroscope sensor 34 configured to provide a gravitational relationship of the endoscope 22. In particular, the gravitational relationship includes the orientation and angular velocity of the camera head unit 12. Preferably, the gyroscope sensor 34 is one of a plurality of electric devices currently known and/or later developed and configured to detect orientation and angular velocity, illustratively including solid state ring lasers, a fiber optic gyroscope and/or a quantum gyroscope. The gyroscope sensor 34 may be mounted to the camera head unit 12 and may detect an acceleration of the camera made in reference to the Earth's gravity. In another embodiment, the orientation unit 30 includes both an accelerometer 32 and a gyroscope sensor 34. Alternatively, the orientation unit 30 may include both an accelerometer 32 and a gyroscope sensor 34.

The orientation unit 30 detects an acceleration and/or a gravitational relationship of the camera and transmits the detected acceleration and/or gravitational relationship to the display control unit 16. The display control unit 16 processes the acceleration and/or gravitational relationship to determine a use. For example, based upon the acceleration or orientation of the camera head unit 12 and/or the endoscope 22, the display control unit 16 may determine that the endoscope 22 is out of the body, and thus determines a non-surgical use, wherein the video image is oriented and maintained in an upright position on the display unit 28. Thus, the video imaging system 10 may use acceleration and/or a gravitational relationship of the camera head unit 12 and/or endoscope 22 to automatically orient the video image in an upright position which allows for rotation of the endoscope 22 as it is being used outside of the body.

In another aspect of the video imaging system 10, the display control unit 16 processes an acceleration and/or a gravitational relationship along with a focal distance to determine a use. For example, a short focal distance and an acceleration below a predetermined acceleration may be processed by the display control unit 16 to determine a surgical use. As used herein, the term "surgical use" refers to the operation of the endo scope 22 within a body. For example, a distance between the lens 24 and an image sensor 26 which is greater than the predetermined distance provides a magnified view, indicating that the object of the image is near. Thus, the display control unit 16 makes a determination that the endoscope 22 is within the body and a surgical use is determined.

With reference again to FIG. 3, an aspect of the video imaging system 10 is provided wherein additional contextual information is provided to further identify the type of surgical use. The video imaging system 10 includes a database stored in memory 36. The database 36 may be stored in the display control unit 16. Any database 36 architecture currently known or later developed may be modified for use herein, illustratively including a computer program unit architecture. The database 36 is configured to store a plurality of surgical procedures, each of the surgical procedures being a surgical use.

The surgical procedures stored in the database 36 may include contextual information relating to the corresponding procedure to include image data and ranges for endoscopic orientation. Each surgical procedure is also associated with a predetermined video image orientation. For instance, a video image displayed on a display unit 28 for a procedure to repair a torn meniscus may be oriented so as to maintain the meniscus along a horizontal axis as described in greater detail below.

Image data may include anatomical features such as a meniscus, a labrum or the like. Image data may also include medical devices such as implants such as a screw, a cage or the like and medical instruments. The display control unit 16 is further configured to process the video image to determine which of the surgical procedures stored in the database 36 is being performed. The display control unit 16 may be further configured to process the video signal so as to maintain the video image in a predetermined video image orientation.

For example, as the endo scope 22 is inserted into a body cavity, the focal distance of the camera head 18 is short, thus the spatial distance between the lens 24 and the image sensor 26 is greater than a predetermined distance, e.g., longer than the lens focal length. The display control unit 16 may determine that the endoscope 22 is being used in a surgical use based solely upon the short focal distance, or may process the short focal distance along with contextual information from the orientation unit 30 to determine that the endoscope 22 is in a surgical use.

Once, the display control unit 16 determines that the endoscope 22 is in a surgical use, the display control unit 16 may process additional contextual information so as to determine which of the plurality of surgical procedures stored in the database 36 is being performed. For example, the display control unit 16 may determine a surgical procedure by processing image data to identify an anatomical feature or a medical device, or by processing the endoscopic orientation. The endoscopic orientation may be determined by the camera head unit 12 by processing the acceleration and/or gravitational relationship of the endo scope 22. It should be appreciated that the display control unit 16 may be programmed to make a determination of a surgical procedure based upon any singular contextual information, e.g., image data or endoscopic orientation of the endo scope 22 or a combination of contextual information.

In another aspect of the present disclosure, the video imaging system 10 includes an input 38. The input 38 may be disposed on the head unit, or the display control unit 16. The input 38 is configured to select any one of the plurality of surgical procedures stored in the database 36. In such an embodiment, the display control unit 16 automatically orients the video signal so as to maintain the video image in an orientation corresponding to the selected surgical procedure.

The display control unit 16 may be programmed with a neural network 40 for learning, wherein the display control unit 16 processes the selected surgical procedure with the contextual information received from the camera head unit 12 to determine if the selected surgical procedure is the same as the surgical procedure determined by the display control unit 16 based off of the contextual information. The database 36 may be updated when a determined surgical procedure is different than a selected surgical procedure.

In another aspect of the present disclosure, the video imaging system 10 includes a second input 42. The second input 42 may be disposed on the head unit, or the display control unit 16. The second input 42 is configured to adjust the orientation of the video image displayed on the display unit 28. This allows the surgeon to set the orientation of the video image to his/her preference. The deviation between what the surgeon selected and what was processed by the display control unit 16 may be stored by the memory 36 and analyzed by the neural network 40 so as to adjust the video image for the same type of surgical procedure performed in the future.

Figure 4A:
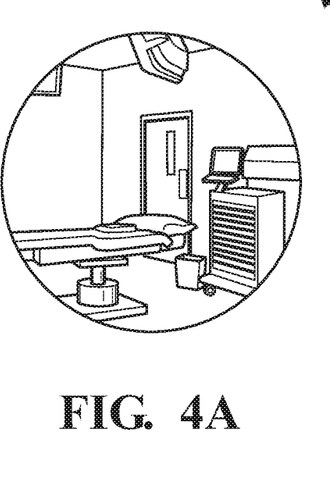
FIG. 4A is a depiction of an image having a long focal distance.
Figure 4B:
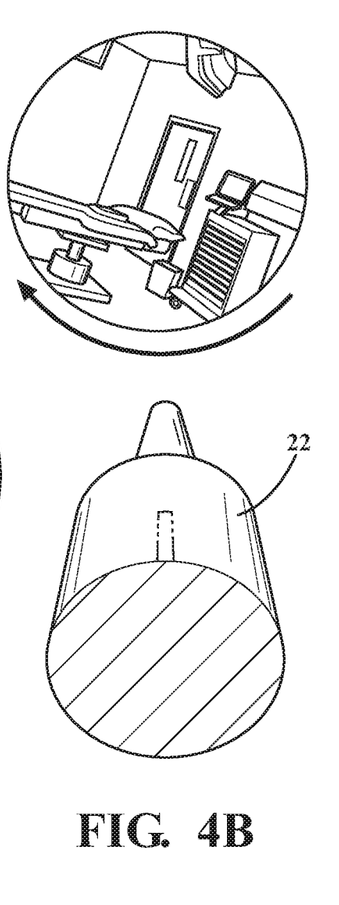
FIG. 4B is a depiction of FIG. 4A showing the image angled.
Figure 4C:
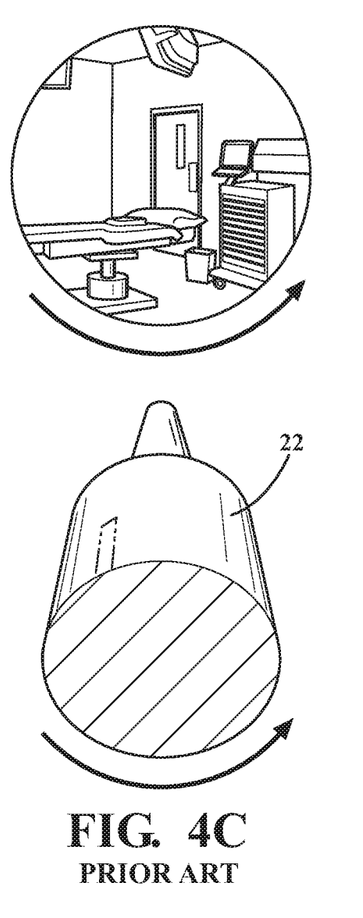
FIG. 4C is a depiction of the prior art method of manually leveling the image shown in FIG. 4B.

With reference now to FIGS. 4A-4D an illustration of an operation of the video imaging system 10 using a focal distance is provided. FIG. 4A provides a video image of the endoscope 22 when the endoscope 22 is held so as to retain the video image in an upright position. FIG. 4A illustrates the upright position. FIG. 4B illustrates an example of an instance, where the nurse holds the endoscope 22 and turns on the endoscope 22. The corresponding video image shows how the nurse is holding the endoscope 22 in a manner which produces a video image which is turned relative to an upright position as indicated by the arrow. In particular, FIG. 4B shows the door being angled. FIG. 4C is a depiction showing the prior art method where, in particular, the nurse has to rotate the endoscope 22 so as to rotate the video image into an upright manner.

Figure 4D:
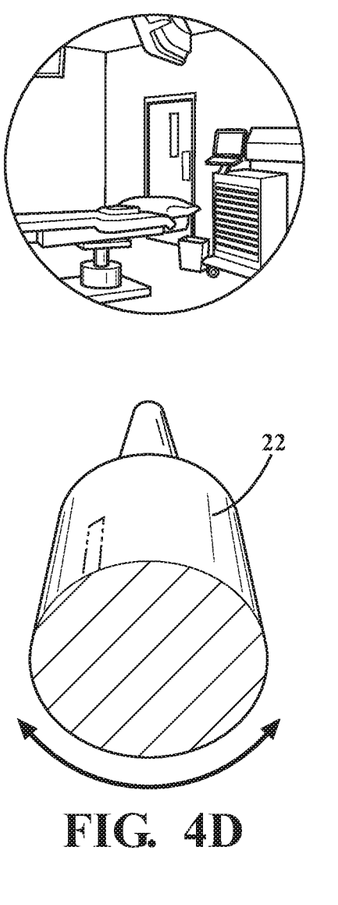
FIG. 4D is a depiction showing the image shown in FIG. 4B being maintained in a predetermined orientation.

As described above, the video imaging system 10 is configured to process a focal distance to automatically orient and maintain the video image in an upright manner. The video image in FIGS. 4A-4D show an example of a long focal distance, as indicated by the focus image of the door. FIG. 4D shows the door and equipment being oriented in the same field of view as seen by a person standing upright in the room. The bi-directional arrow beneath the endoscope 22, shown in FIG. 4D, indicates a rotation of the endoscope 22. However, the video image remains upright. Thus, by processing at least a focal distance, the video imaging system determines a non-surgical use and the video image on the display unit 28 is maintained in an upright manner regardless of the rotation of the endoscope 22.

As described above, the focal distance may be determined by the aperture and the lens focal length. The lens focal length may be determined by a spatial displacement between the lens 24 and the image sensor 26. The video image of FIG. 4D shows the focus is set to infinity, indicating that the spatial distance between the lens 24 and image sensor 26 is spaced apart from each other by less than, or equal to, a predetermined distance. The display control unit 16 may process the distance between the lens 24 and the image sensor 26 based upon the actual distance which may be detected by a sensor such as a transducer mounted to the moving element, or by processing the position of the dial or actuation of a button which controls the focus. The display control unit 16 processes the spatial distance so as to determine that the endoscope 22 is in a non-surgical use and processes the video signal so as to maintain the video image in an upright manner. Thus, as the endo scope 22 is rotated, as indicated by the bi-directional arrow in FIG. 4D, the video image remains upright on the display. As described above, the rotation may be done by an individual, or when endo scope 22 is handed over to the surgeon.

The video imaging system 10 may process other contextual information gathered by the orientation unit 30 to determine the use. For instance, when the orientation unit 30 determines that the endoscope 22 is subject to a large acceleration which is not commensurate with surgical use, but determines that the focal distance is short, the display control unit 16 determines that the endoscope 22 is in a non-surgical use. Such a scenario may be commensurate with the nurse or surgeon cleaning the lens 24.

Figure 5A:
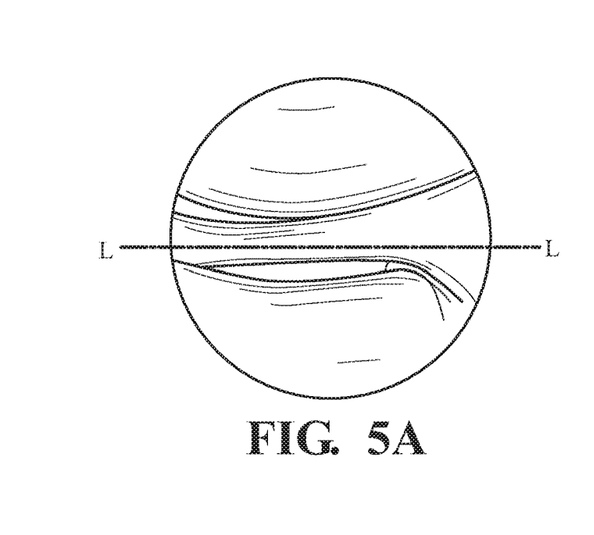
FIG. 5A is a depiction of an image having a short focal distance.
Figure 5B:
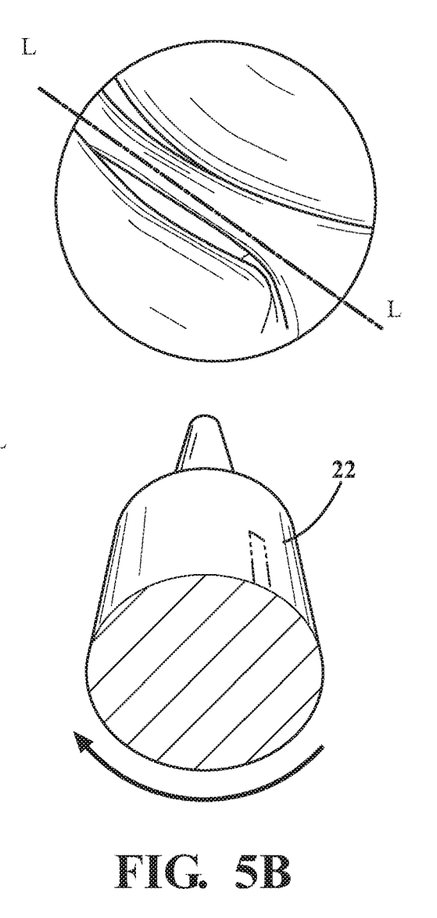
FIG. 5B is a depiction of FIG. 5A showing the image angled.
Figure 5C:
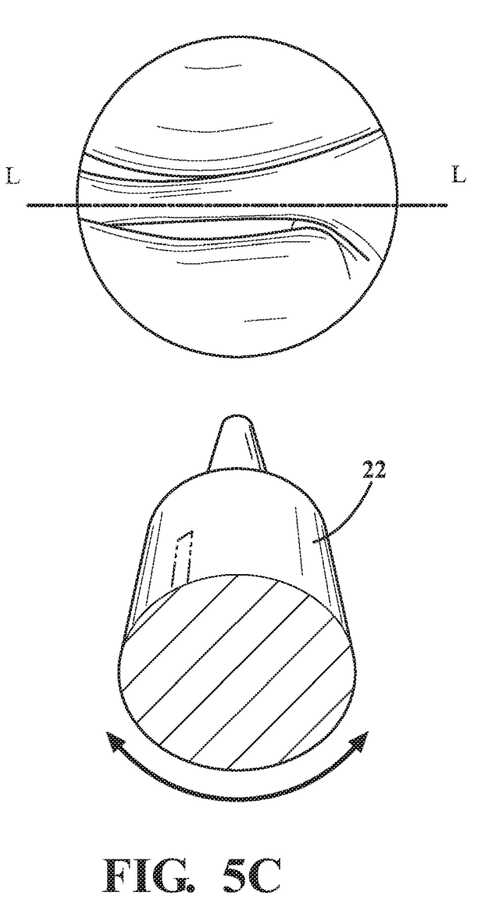
FIG. 5C is a depiction showing the image shown in FIG. 5B being maintained in a predetermined orientation.

With reference now to FIGS. 5A-5C an illustration of an operation of the video imaging system 10 using other contextual imaging to orient the video image is provided. FIGS. 5A-5C show an illustration of a short focal distance. For illustrative purposes, the illustration is provided in the context of a procedure to correct a meniscus. FIG. 5A shows the meniscus in a preferred orientation wherein the longitudinal length, indicated by line "L-L" of the meniscus is generally is aligned with the horizon.

FIG. 5B shows an example of the video image taken by the endoscope 22 that is made without any correction, or leveling. This may result from the difference between how the video imaging was leveled to an upright position by the display control unit 16 when a non-surgical use was determined. As the endoscope 22 is inserted into the body, the focal distance is changed from a long focal distance to a short focal distance. As such, the distance between the lens 24 and the image sensor 26 is equal to or greater than the predetermined distance. The display control unit 16 process the distance between the lens 24 and the image sensor 26 to determine that the endoscope 22 is in a surgical procedure.

The video imaging system 10 is configured to process additional contextual information to determine what type of surgical use, e.g., the type of surgical procedure being performed. The contextual information that may be processed includes image data and/or ranges for endoscopic orientation. For instance, the approach angle of the endoscope 22 may be determined by the orientation unit 30 and may be processed in conjunction with image data to determine the type of surgical procedure that is being performed. For illustrative purposes, FIGS. 5B and 5C will be described wherein image data is processed by the display control unit 16 to determine the type of surgical procedure being performed.

As described above, the database 36 stores a plurality of surgical procedures. The surgical procedures may include contextual information relating to the corresponding procedure to include image data and ranges for endoscopic orientation. In this case, the image of a meniscus is associated with one of a plurality of medical procedures to include a procedure to correct a radial tear, a horizontal tear, flap tear or the like. Each of these tears may also include a stored range of endoscopic orientations, wherein the display control unit 16 processes the video image to identify a meniscus. The type of the meniscus procedure may be determined based upon the endoscopic orientation, wherein the actual orientation of the endoscope 22 may also be processed by the display control unit 16 to confirm which of the types of meniscus procedures is being performed. The actual orientation of the endoscope 22 may be determined by information gathered by the orientation unit 30.

Once the display control unit 16 identifies the meniscus, the video image is leveled, or oriented, to a predetermined orientation, as shown in FIG. 5C. FIG. 5C also depicts how the video image remains leveled even when the endo scope 22 is rotated. It should be appreciated that other image data, such as a medical implant or a tool may be stored in the database 36 and processed by the display control unit 16 to determine the type of surgical procedure being performed, which also levels and maintains the video image in accordance with the orientation associated with said medical procedure.

The video imaging system 10 may include an input 38. The input 38 is configured to select any one of the plurality of surgical procedures stored in the database 36. In such an embodiment, the display control unit 16 automatically orients the video signal so as to maintain the video image in an orientation corresponding to the selected surgical procedure even when the endoscope 22 is rotated, as illustratively shown in FIG. 5C. The video imaging shown on the display unit 28 may be manually rotated by the user by actuation of a second input in instances where the surgeon prefers an orientation different than what was leveled by the display control unit 16.

As described above, the display control unit 16 may be programmed with a neural network 40 for learning. In some implementations, the display control unit 16 processes the selected surgical procedure with the contextual information received from the camera head unit 12 to determine if the selected surgical procedure is the same as the surgical procedure determined by the display control unit 16 based off of the contextual information. In particular, the neural network 40 may process a selected surgical procedure (e.g., a surgical procedure selected by the input 38 from the plurality of surgical procedures stored in the database 36) with a determined surgical procedure (e.g., the surgical procedure determined by the display control unit 16 based off of the contextual information) and update the contextual information in the database 36 with actual contextual information of the selected surgical procedure when the determined surgical procedure is different than the selected surgical procedure.

A number of implementations have been described. Nevertheless, it will be understood that various modifications may be made without departing from the spirit and scope of the disclosure. Accordingly, other implementations are within the scope of the following claims.

What is claimed is:

1. A video imaging system operable to display a video image onto a display, the video imaging system comprising:
   an endoscope;
   a camera head unit;
   a camera control unit configured to determine a focal distance;
   an orientation unit disposed on the camera head unit, the orientation unit configured to detect at least one of an acceleration and a gravitational relationship of the endoscope; and
   a display control unit configured to process the focal distance and the acceleration and the gravitational relationship of the endoscope so as to determine the use, wherein the display control unit determines that the endoscope is in a non-surgical use in instances where the focal distance is greater than a predetermined distance and the acceleration is greater than or equal to a predetermined acceleration and determines that the endoscope is in a surgical use when the focal distance is less than the predetermined distance and the acceleration is less than the predetermined acceleration, wherein the display control unit is further configured to process the surgical use and non-surgical use to maintain the video image in a predetermined orientation.

2. The video imaging system as set forth in claim 1, wherein the camera head unit includes a lens and an image sensor, the lens and the image sensor configured to move relative to each other, the camera head unit configured to control a displacement of the image sensor relative to the lens so as to focus the video image when there is a change in the focal distance.

3. The video imaging system as set forth in claim 1, wherein the orientation unit includes an accelerometer.

4. The video imaging system as set forth in claim 1, wherein the orientation unit includes a gyroscope sensor.

5. The video imaging system as set forth in claim 1, wherein the predetermined distance is 10 cm.

6. The video imaging system as set forth in claim 1, further including a database, the database storing a plurality of surgical procedures, each of the plurality of surgical procedures having a video predetermined orientation, and each of the plurality of surgical procedures being a surgical use.

7. The video imaging system as set forth in claim 6, wherein each of the plurality of surgical procedures stored in the database includes contextual information, the contextual information including an image data.

8. The video imaging system as set forth in claim 7, wherein the display control unit processes image data with the video image so as to determine which of the surgical procedures of the plurality of surgical procedures is being performed and processes the video image so as to maintain the video image in the predetermined video orientation.

9. The video imaging system as set forth in claim 7, wherein the contextual information includes a range for an endoscopic orientation, the camera head unit configured to process the at least one of the acceleration and the gravitational relationship of the endoscope so as to determine an endoscopic orientation, the display control unit further configured to process the endoscopic orientation to determine a surgical procedure.

10. The video imaging system as set forth in claim 6, further including an input, the input configured to select one of the plurality of surgical procedures, the display control unit configured to process the selected surgical procedure so as to maintain the video image in the predetermined orientation.

11. The video imaging as set forth in claim 9, further including a neural network, the neural network configured to process a selected surgical procedure of the plurality of surgical procedures with the determined surgical procedure and update the contextual information with actual contextual information of the selected surgical procedure.

12. The video imaging system as set forth in claim 11, further including a second input, the second input configured to manually adjust an orientation of the video image to a preferred orientation, wherein the neural network is configured to process the preferred orientation.

13. A method for displaying a video image onto a display, the method comprising:
    determining, with a camera control unit, a focal distance;
    detecting, with an orientation unit, at least one of an acceleration and a gravitational relationship of the endoscope; and
    processing, with a display control unit, the focal distance and the acceleration and the gravitational relationship of the endoscope so as to determine a surgical use and a non-surgical use, wherein the surgical use being when the focal distance is less than a predetermined distance and the acceleration is less than the predetermined acceleration and the non-surgical use being when the focal distance is greater than the predetermined distance and the acceleration is equal to or greater than the predetermined acceleration;
    processing, with the display control unit, the surgical use and the non-surgical use to maintain the video image in a predetermined orientation.

14. The method as set forth in claim 13, wherein a camera head unit includes a lens and an image sensor, the method further comprising:
    moving the lens relative to the image sensor;
    controlling, with the camera head unit, a displacement of the image sensor relative to the lens so as to focus the video image when there is a change in the focal distance.

15. The method as set forth in claim 13, further comprising:
    storing, in a database, a plurality of surgical procedures, each of the plurality of surgical procedures having a video predetermined orientation, and each of the plurality of surgical procedures being the surgical use.

16. The method as set forth in claim 15, wherein each of the plurality of surgical procedures stored in the database includes contextual information, the contextual information including an image data.

17. The method as set forth in claim 16, further comprising:
    processing, with the display control unit, image data with the video image;
    determining, with the display control unit, which of the surgical procedures of the plurality of surgical procedures is being performed; and
    processing, with the display control unit, the video image so as to maintain the video image in the predetermined video orientation.

18. The method as set forth in claim 16, further comprising:
    processing, with the camera head unit, a range for an endoscopic orientation;
    processing, with the camera head unit, the at least one of the acceleration and the gravitational relationship of the endoscope so as to determine an endoscopic orientation; and processing, with the display control unit, the endoscopic orientation to determine a surgical procedure.

* * * * *